United States Patent [19]

Smith et al.

[11] Patent Number: 5,132,482
[45] Date of Patent: Jul. 21, 1992

[54] PROCESS FOR THE OXIDATIVE COUPLING OF METHANE TO HIGHER HYDROCARBONS

[75] Inventors: Kevin J. Smith, Edmonton; Jan Z. Galuszka, Nepean, both of Canada

[73] Assignee: Alberta Research Council, Edmonton, Canada

[21] Appl. No.: 537,703

[22] Filed: Jun. 14, 1990

[51] Int. Cl.$^5$ .............................................. C07C 2/00
[52] U.S. Cl. ....................... 585/500; 585/415; 585/417; 585/418; 585/541; 585/654; 585/656; 585/658; 585/661; 585/700; 585/943
[58] Field of Search ............. 585/415, 417, 418, 500, 585/541, 654, 656, 658, 661, 700, 943

[56] References Cited

U.S. PATENT DOCUMENTS

| | | | |
|---|---|---|---|
| 4,499,323 | 2/1985 | Gaffney | 585/943 |
| 4,523,050 | 6/1985 | Jones et al. | 585/943 |
| 4,665,259 | 5/1987 | Brazdil et al. | 585/943 |

FOREIGN PATENT DOCUMENTS 3644167 7/1988 Fed. Rep. of Germany.

Primary Examiner—Patrick P. Garvin
Assistant Examiner—E. D. Irzinski
Attorney, Agent, or Firm—Dressler, Goldsmith, Shore, Sutker & Milnamow, Ltd.

[57] ABSTRACT

An improvement in the process for the oxidative coupling of methane is provided. Typically, the reaction takes place in a reactor that includes a catalyst zone. A primary $CH_4/O_2$ stream is fed into the entrance of the reactor and reacted at a temperature of 600° C.–1000° C. and a pressure of between 101 kPa and 800 kPa. The improvement comprises introducing an auxiliary oxygen stream directly into the catalyst zone and one or more points to thereby selectively increase the yield of $C_{2+}$ products.

4 Claims, 1 Drawing Sheet

PROCESS FOR THE OXIDATIVE COUPLING OF METHANE TO HIGHER HYDROCARBONS

FIELD OF THE INVENTION

The present invention relates to an improvement in the process for the oxidative coupling of methane to higher hydrocarbons.

BACKGROUND OF THE INVENTION

The oxidative condensation reaction of methane is conventionally termed the oxidative coupling of methane. This method allows production of ethane, ethylene and usually small amounts of higher hydrocarbons (hereinafter referred to as $C_{2+}$) from methane. Deleteriously, however, the total oxidation of methane to water and oxides of carbon usually accompanies the oxidative coupling reaction.

Typically, a tubular fixed bed reactor is utilized in which to carry out the reaction Two different procedures for feeding the reactant gases into the reactor have been used in prior art processes. In the first case, oxygen and methane were introduced at the entrance of the tubular reactor in a cycling mode. Thus, oxygen only was fed to the reactor for a given period, followed by inert gas and subsequently, methane only was fed to the reactor for a given period. In the second case, oxygen and methane were introduced at the entrance of the tubular reactor simultaneously. Thus $CH_4$ and $O_2$ were co-fed to the reactor unit.

The oxidative coupling of methane has been extensively studied during recent years. In particular, the development of catalysts functional to enhance $C_{2+}$ yield has been of interest More specifically, catalysts have been prepared which have included most elements of the periodic table and/or their oxides, and/or their salts thereof, either singly or in admixture. It has been determined with all the known catalysts investigated that an apparent limit to the yield of $C_{2+}$ of about 25% exists mainly because of the role of the gas phase reactions.

Higher $C_{2+}$ yields in oxidative coupling of methane are obtainable by increasing the methane conversion or the $C_{2+}$ selectivity or both. Unfortunately, higher selectivity is usually observed at lower conversion for this process The selectivity is the most important factor in the practical application of the coupling reaction. If the selectivity is high a high $C_{2+}$ yield may be achieved by recycling the reactants.

Exemplary prior art processes are described in U.S. Pat. Nos. 4,523,049, 4,523,044, 4,665 259, 4,560,821, 4,523,050 or 4,499,323. It would be advantageous if a process could be found which would overcome the limitative yield which occurs with these prior art processes.

SUMMARY OF THE INVENTION

In accordance with the present invention, it has been discovered that the higher $C_{2+}$ selectivity may be achieved by introduction of an auxiliary oxygen stream into the reactor. Furthermore, said auxiliary oxygen stream is to be introduced into a particular catalyst zone of the reactor. Any space in the reactor containing catalyst in any form defines a catalyst zone Preferably the auxiliary oxygen stream would be introduced at a plurality of points, rather than just at one location of the reactor. More specifically, by introducing auxiliary oxygen directly into the catalyst zone of the reactor, increased yields of ethane and ethylene are obtained (hereinafter referred to as $C_2$). In a second embodiment of the invention, it has been found that increased yields of $C_{2+}$ products may also be obtained by introducing the auxiliary oxygen stream at the lower end of the catalyst zone and/or therebeneath.

In a first broad aspect, the invention relates to a process for oxidatively coupling methane wherein a reactor is provided and a primary $CH_4/O_2$ stream is fed into the entrance of the reactor and reacted at a temperature of 600° C. to 1000° C. and a pressure of between 101 kPa and 800 kPa, the improvement which comprises introducing an auxiliary oxygen stream directly into the catalyst zone at one or more points to thereby selectively increase the yield of $C_{2+}$ products.

In a second broad aspect there is provided an improvement in a process for oxidatively coupling methane wherein a reactor is provided and a primary $CH_4/O_2$ stream is fed into the entrance of the reactor which comprises introducing an auxiliary oxygen stream at the lower end of the catalyst zone and/or therebeneath to thereby selectively increase the yield of $C_{2+}$ hydrocarbons.

DESCRIPTION OF THE PREFERRED EMBODIMENT

Figure 1:
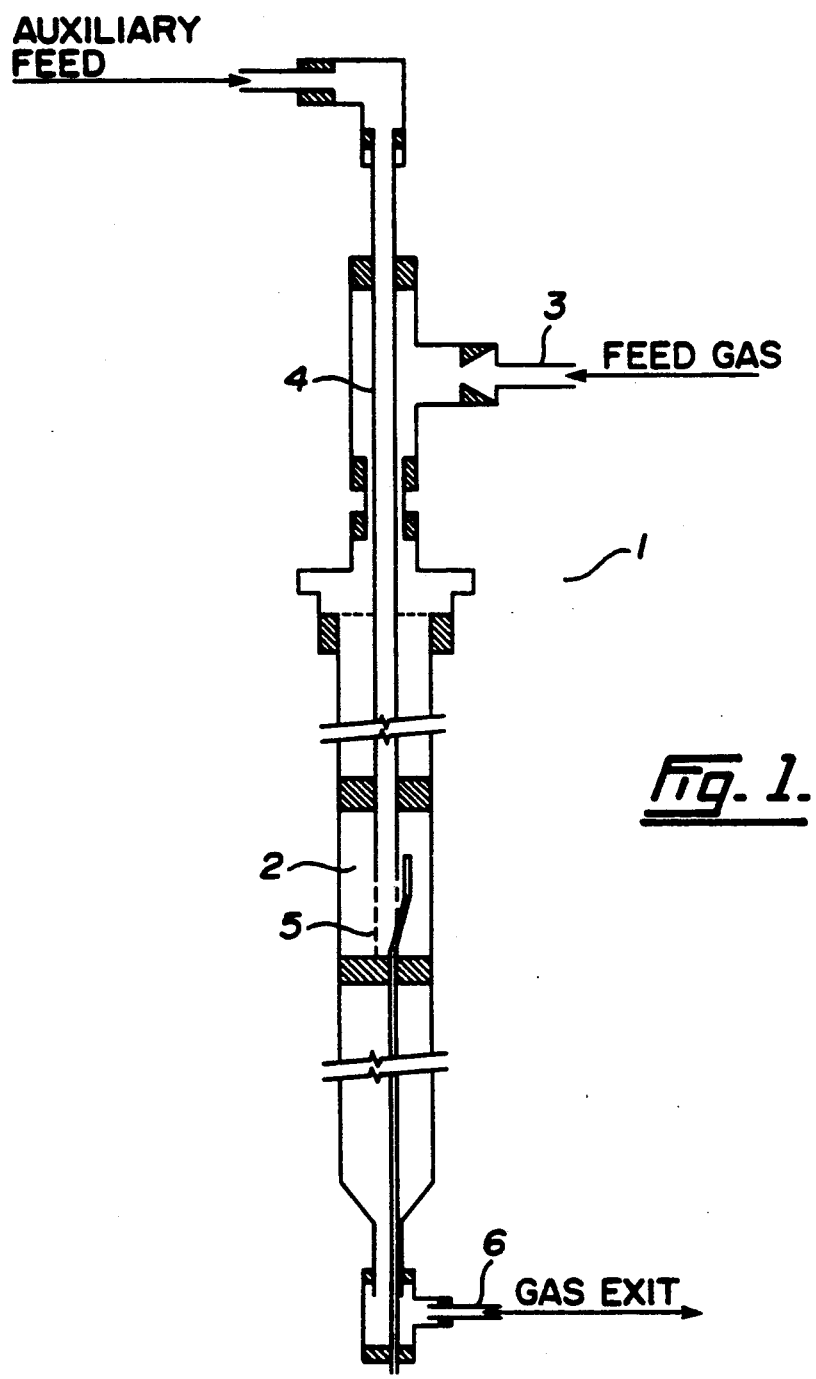
FIG. 1 illustrates a typical reactor for use in the practise of the present invention.

Having reference to the accompanying drawing there is shown a fixed bed tubular reactor 1. A catalyst bed 2 is provided within the reactor. A port 3 for the introduction of feed gas is provided A conduit 4 extends downwardly into the catalyst bed 2, defining ports 5, for the injection of auxiliary oxygen thereto. Following the oxidative coupling reaction, the products yielded leave the reactor via exit 6. The ports 5 would typically be at the mid-point of the catalyst bed and at the end thereof.

The feed gas may typically comprise $CH_4/O_2$ having a ratio greater than one. Alternatively the feed gas may comprise methanol with different oxidants including NO, $N_2O$ and Natural Gas/Oxygen and Natural Gas/Air.

The number of catalysts which have been described and tested in the literature and patents is extensive. Amongst the catalysts tested were those detailed in Table I herebelow.

TABLE I

Catalyst $Sm_2O_3$
$Ba/CeO_2$
$Li/BeO$
$Sr/La_2O_3$
$PbO/Al_2O_3$
$LaAlO_3$
$Nd_2O_3$
$K_2CO_3/Bi_2O_3/Al_2O_3$
$NaCL/Mn$-oxide
$Na_2CO_3/CaO$
$Mn/Na_4P_2O_7/SiO_2$
$Li/MgO$
$BaO/CaO$
$Li/TiO_2$ PbO/Al$_2$O$_3$
Na/Pr$_6$O$_{11}$
SrCe$_{0.90}$Yb$_{0.10}$O$_{2.95}$
PbO/MgO
MgCl$_2$/CaO
SrZrO$_3$
K/Sb$_2$O$_4$
LiCl/MnO$_2$
Li$_2$CO$_3$/Sm$_2$O$_3$
Ca/layered bismuth oxychloride
Li/ZnO Na/CaO
Na/MgO
K/BaCO$_3$
K/Bi$_2$O$_3$/Al$_2$O$_3$ So when one states that a catalyst is present it is to be understood that the catalyst would be one suitable for the oxidative coupling reaction to take place.

Possible auxiliary gases would include O, CH$_4$, air, or O$_2$/CH$_4$ mixtures or natural gas (80-90%) in admixture with air. Selection of the gas and its concentration would be within the skill of the art.

Typical reaction conditions would range from 700°-750° C. although the range could be broadened to 600°-1000° C. The pressure would range from 101 kPa to 800 kPa. Residence time in the reactor 1 would be about two seconds.

EXPERIMENTAL

The following examples are included to demonstrate the operability of the present invention.

EXAMPLE 1

In this example a Li$_2$O/PbO/CaO catalyst of nominal composition 7:20:73 weight % was tested at 101 kPa and 700° C. with auxiliary gas added to the midpoint of the catalyst bed (Location 1, FIG. 1). The main feed gas was fed to the reactor at a rate of 50 mL/min. and had a nominal composition He:CH$_4$:O$_2$ equal to 80:13:7 volume %. The auxiliary gas was fed to the reactor at the rate of 50 mL/min. with a nominal composition He:O$_2$ equal to 93:7 volume %. Helium is present in both feed gas streams to control the formation of explosive mixtures of CH$_4$ and O$_2$. A comparative activity test was also performed in which the auxiliary gas consisted of pure He only, all other conditions being exactly the same.

The results from the two experiments are shown in Table II herebelow (Runs 2 and 3). The data clearly indicates that with addition of oxygen at the midpoint of the reactor the C$_{2+}$ STY increases from $0.096 \times 10^{-6}$ mole/g.catalyst/sec. to $0.14 \times 10^{-6}$ mole/g.catalyst/sec., representing an increase of 47% in C$_{2+}$ production rate. Furthermore, the selectivity to ethylene increases as shown by the increase in the ethylene/ethane ratio from 0.8 to 1.2.

Table II also presents data for the case where the total moles fed to the reactor via the main feed stream with no auxiliary feed gas is equivalent to the total moles fed via the main feed stream plus the auxiliary feed stream (Runs 1 and 3). In this case the C$_{2+}$ STY increases from $0.121 \times 10^{-6}$ moles/g.catalyst/sec. to $0.141 \times 10^{-6}$ moles/g.catalyst/sec. representing a 16% increase in C$_{2+}$ STY.

TABLE II

REACTOR CONFIGURATION EFFECTS ON OXIDATIVE COUPLING OF METHANE

Catalyst: Li$_2$O/PbO/CaO
Conditions: 700° C., 101 kPa
Auxiliary gas addition at the mid-point of catalyst bed (Location 1, FIG. 1)

| | Primary Feed | | | Auxiliary Feed | | | | |
|---|---|---|---|---|---|---|---|---|
| Run No. | Total Flow mL/min. | CH$_4$ % | O$_2$ % | Total Flow mL/min. | O$_2$ % | CH$_{2+}$ STY mol/g.cat./sec. | C$_2$=/C$_2$ Ratio | CH$_4$ Conversion % |
| 1 | 100 | 7 | 7 | — | — | 0.123 | 0.90 | 30 |
| 2 | 50 | 13 | 7 | 50 | — | 0.098 | 0.83 | 30 |
| 3 | 50 | 13 | 7 | 50 | 7 | 0.142 | 1.19 | 37 |

EXAMPLE 2

In this example a La$_2$O$_3$PbO/CaO catalyst of nominal composition 20:73 weight % was tested at 101 kPa and 700° C. with auxiliary gas added at the midpoint of the catalyst bed (Location 1, FIG. 1). The main feed gas was fed to the reactor at a rate of 50 mL/min. and nominal composition He:CH$_4$:O$_2$ equal to 80:13:7 volume %. The auxiliary gas was fed to the reactor at the rate of 50 mL/min. with nominal composition He:O$_2$ equal to 93:7 volume % (Run 5). He is present in both feed gas streams to control the formation of explosive mixtures of CH$_4$ and O$_2$. The results obtained from this experiment are compared to the case with no auxiliary gas addition (Run 4) but with the total moles of each component fed to the reactor equal to Run 5. The results shown in Table III indicate an increase in C$_{2+}$ STY from $0.034 \times 10^{-6}$ mole/g.catalyst/sec. to $0.054 \times 10^{-6}$ mole/g.catalyst/sec. representing an increase of 64% in C$_{2+}$ STY.

TABLE III

REACTOR CONFIGURATION EFFECTS ON OXIDATIVE COUPLING OF METHANE

Catalyst: La$_2$O$_3$/PbO/CaO
Conditions: 700° C., 101 kPa
Auxiliary gas addition at exit of catalyst bed (Location 2, FIG. 1).

| | Primary Feed | | | Auxiliary Feed | | C$_{2+}$ STY | |
|---|---|---|---|---|---|---|---|
| Run No. | Total Flow mL/min. | CH$_4$ % | O$_2$ % | Total Flow mL/min. | O$_2$ % | mol/ g.cat./ sec. | CH$_4$ Conversion % |
| 4 | 100 | 7 | 7 | — | — | 0.033 | 50 |
| 5 | 50 | 13 | 7 | 50 | 7 | 0.054 | 56 |

EXAMPLE 3

In this example a Li$_2$O/MgO catalyst of nominal composition 7:93 weight % was tested at 101 kPa and 700° C. with auxiliary gas added at the end of the catalyst bed (Location 2, FIG. 1). The main feed gas was fed to the reactor at a rate of 50 mL/min. and nominal composition He:CH$_4$:O$_2$ equal to 80:13:7 volume %. The auxiliary gas was fed to the reactor at the rate of 50 mL/min. with nominal composition He:O$_z$ equal to 93:7 volume % (Run 7). He is present in both feed gas streams to control the formation of explosive mixtures of CH$_4$ and O$_2$. The results obtained from this experiment are compared to the case with no auxiliary gas addition (Run 6) but with the total moles of each component fed to the reactor equal to Run 7. The results shown in Table IV indicate an increase in C$_{2+}$ STY from $0.030 \times 10^{-6}$ mole/g.catalyst/sec. to $0.048 \times 10^{-6}$ mole/g.catalyst/sec. representing a 60% increase in C$_{2+}$ STY.

TABLE IV

REACTOR CONFIGURATION EFFECTS ON COUPLING OF METHANE

Catalyst: Li$_2$O/MgO
Conditions: 700° C., 101 kPa
Auxiliary gas addition at exit of
catalyst bed (Location 2, FIG. 1).

| Run No. | Primary | | | Auxiliary Feed | | C$_{2+}$ STY | |
|---|---|---|---|---|---|---|---|
| | Total Flow mL/min. | CH$_4$ % | O$_2$ % | Total Flow mL/min. | O$_2$ % | mol/ g.cat./ sec. | CH$_4+$ Conversion % |
| 6 | 100 | 7 | 7 | — | — | 0.030 | 8 |
| 7 | 50 | 13 | 7 | 50 | 7 | 0.048 | 10 |

The embodiments of the invention in which an exclusive property or privilege is claimed are defined as follows:

1. In a process for oxidatively coupling methane wherein a reactor is provided which reactor defines a catalyst zone and a primary CH$_4$/O$_2$ feed stream is fed into the entrance of the reactor and reacted at a temperature of 600° C. to 1000° C. and a pressure of between 101 kPa and 800 kPa, the improvement which comprises introducing an auxiliary oxygen stream directly into the catalyst zone at one or more points to thereby selectively increase the yield of C$_{2+}$ products.

2. The process as set forth in claim 1 wherein the auxiliary oxygen stream is introduced at the lower end of the catalyst zone.

3. The process as set forth in claim 1 wherein said auxiliary oxygen stream is introduced beneath said catalyst zone.

4. The process as set forth in claims 1, 2 or 3 wherein the source of CH$_4$ in said feed stream is CH$_4$ or natural gas and wherein the source of O$_2$ in said feed stream is O$_2$ or air.

* * * * *